United States Patent
Boissonneault et al.

(10) Patent No.: US 6,667,050 B1
(45) Date of Patent: Dec. 23, 2003

(54) CHEWABLE ORAL CONTRACEPTIVE

(75) Inventors: Roger M. Boissonneault, Long Valley, NJ (US); Tina M. deVries, Long Valley, NJ (US)

(73) Assignee: Galen (Chemicals) Limited, Dunlaoghaire (IE)

( * ) Notice: Subject to any disclaimer, the term of this patent is extended or adjusted under 35 U.S.C. 154(b) by 0 days.

(21) Appl. No.: 09/879,028

(22) Filed: Jun. 12, 2001

Related U.S. Application Data

(63) Continuation-in-part of application No. 09/286,908, filed on Apr. 6, 1999.

(51) Int. Cl.[7] ............................................. A61K 47/00

(52) U.S. Cl. ...................... 424/439; 424/400; 424/440; 424/441; 424/464; 424/484; 424/489; 514/841; 514/843

(58) Field of Search ................................ 424/400, 439, 424/440, 441, 464, 484, 489; 514/841, 843

(56) References Cited

U.S. PATENT DOCUMENTS

| | | | |
|---|---|---|---|
| 3,960,911 A | 6/1976 | Suschitzky et al. | |
| 4,036,983 A | 7/1977 | Rutherford et al. | |
| 4,038,413 A | 7/1977 | Suschitzky et al. | |
| 4,136,162 A | 1/1979 | Fuchs et al. | |
| 4,512,986 A | 4/1985 | Reel et al. | |
| 4,684,534 A | 8/1987 | Valentine | |
| 5,135,744 A | 8/1992 | Alexander et al. | |
| 5,569,456 A | 10/1996 | Gorinskyt | |
| 5,576,014 A | 11/1996 | Mizumoto et al. | |
| 5,747,480 A | * | 5/1998 | Gast .......................... 514/170 |

* cited by examiner

*Primary Examiner*—Thurman K. Page
*Assistant Examiner*—Charesse Evans
(74) *Attorney, Agent, or Firm*—Akin, Gump, Strauss, Hauer & Feld, L.L.P.

(57) ABSTRACT

The present invention relates to a chewable, palatable oral contraceptive tablet, comprising an oral contraceptive agent, a chewable carrier suitable for human consumption, and not comprising a ferrocene compound, as well as use of these tablets in a method of human female oral contraception, and in a method of enhancing compliance with a human female oral contraceptive regimen.

60 Claims, No Drawings

CHEWABLE ORAL CONTRACEPTIVE

CROSS-REFERENCE TO RELATED APPLICATIONS

This is a continuation-in-part of U.S. patent application Ser. No. 09/286,908, filed Apr. 6, 1999.

STATEMENT REGARDING FEDERALLY SPONSORED RESEARCH OR DEVELOPMENT

Not Applicable.

REFERENCE TO MICROFICHE APPENDIX

Not Applicable.

BACKGROUND OF THE INVENTION

The present invention generally relates to an oral contraceptive delivery system, and in particular an oral contraceptive delivery system involving novel alternate dose forms to improve compliance.

The efficacy of oral contraceptives tends to be particularly patient compliance dependent, largely due to the lack of a disease state or symptoms to remind a human female patient (sometimes referred to simply as "patient" or "woman") to take a pill. The single most significant reason for failure with oral contraceptives is use, rather than method, failure. That is, unless the contraceptives are used according to the prescribed regimen, the contraceptives can fail to effectively help a patient avoid pregnancy. Further, in order to be most effective in preventing pregnancy and maintaining menstrual cycle control, proper compliance with an oral contraceptive dosage regimen requires that the oral contraceptives be taken at about the same time each day.

Various attempts have been made to improve patient compliance with contraceptive regimens. For example, it has been suggested that progestin rods can be inserted subdermally. This procedure has been described, for example, in U.S. Pat. No. 5,756,115. This technique has the significant disadvantage of requiring a surgical incision, a procedure that is highly disfavored by a relatively large segment of the patient population.

As another example, it has been suggested that DEPO-PROVERA® (Pharmacia, Inc.) medroxyprogesterone acetate can be injected subcutaneously every three months. This technique has been described, for example, in U.S. Pat. No. 4,639,439. This procedure has the disadvantage of requiring an injection via hypodermic needle, which is also a procedure that is disfavored by many patients.

In many cases, the patient prefers to carry the contraceptive pills on her person as a matter of lifestyle or personal discretion. This is especially true for younger patients, and it is not uncommon for such patients to exchange pills. Members of this population tend to view portable packaging of the pills, immediate access to the pills, and ease of pill use as significant benefits.

Prior proposed solutions to the compliance problem have tended to focus primarily or exclusively on optimizing compliance packaging, rather than on changes to the dosage form. It has been suggested that instead of being packaged in vials, contraceptive pills can be packaged in 21 or 28 day blister packages. It has also been suggested that the size of these packages can be reduced to improve portability and confidentiality.

Although oral contraceptive pills provided in a small blister package are somewhat more convenient to carry and to conceal, they are not necessarily easy to ingest. Access to water to facilitate contraceptive pill taking remains a problem. Most medications are typically stored in a medicine cabinet and therefore are likely to be near a water source. On the contrary, oral contraceptive pills are often carried on the person and a source of water is not always available when it is time to take the oral contraceptive pill. Additionally, a certain segment of the patient population will have trouble swallowing pills, irrespective of access to water.

The present invention provides an improved oral contraceptive tablet. The technology encompassed in the invention involves a chewable, palatable oral contraceptive tablet that has appropriate size and hardness for blister packaging and compliant use.

BRIEF SUMMARY OF THE INVENTION

One aspect of the present invention relates to a chewable, palatable oral contraceptive tablet, comprising an oral contraceptive agent, a chewable carrier suitable for human consumption, and not comprising a ferrocene compound.

Another aspect of this invention relates to a method of human female oral contraception, the method comprising providing a chewable, palatable oral contraceptive tablet comprising a contraceptively effective amount of an oral contraceptive agent, and a chewable carrier suitable for human consumption, and not comprising a ferrocene compound, and administering the tablet to a human female.

Yet another aspect of this invention relates to a method of enhancing compliance with a human female oral contraceptive regimen involving oral contraceptive tablets, the method comprising providing chewable, palatable oral contraceptive tablets comprising a contraceptively effective amount of an oral contraceptive agent, and a chewable carrier suitable for human consumption, and not comprising a ferrocene compound, and administering the tablets to the human female in accordance with the contraceptive regimen.

BRIEF DESCRIPTION OF THE SEVERAL VIEWS OF THE DRAWINGS

Not Applicable.

DETAILED DESCRIPTION OF THE INVENTION

The present invention relates to chewable, palatable oral contraceptive tablets for administering an oral contraceptive agent to human females. The tablets of this invention may simply be chewed, and therefore are easy for a patient to ingest, even in the absence of a liquid. The oral contraceptive agent formulation of this invention improves dosage regimen compliance, and thereby enhances the desired contraceptive effect of the oral contraceptive. This invention also includes methods for administering the oral contraceptive formulations to a woman.

Definitions

The articles "a" and "an" are used herein to refer to one or more than one (i.e., to at least one) of the grammatical objects of the article. By way of example, "an element" means one element or more than one element.

The term "oral contraceptive agent," as used herein, refers to any compound or combination of compounds which, when administered orally, prevents pregnancy.

The term "estrogen," as used herein, refers to any natural or synthetic compound which exhibits an effect on the female reproductive organs in a manner similar to the natural female hormone estrogen. Examples of an estrogen include, but are not limited to, ethinyl estradiol, estradiol, estradiol valerate, and estradiol acetate.

The term "progestin," as used herein, refers any natural or synthetic compound which exhibits a progestational effect on the female reproductive organs. Examples of a progestin include, but are not limited to, norethindrone, norethindrone acetate, desogestrel, levonorgestrel, ethynodiol diacetate, norgestrel, norgestimate, gestodene, drospirenone, trimegestone, levodesogestrel, gestodyne and nesterone.

The term "palatable," as used herein, means that the tablet of this invention has a taste, mouth feel, chewability, texture, aroma, and lack of grittiness and bad aftertaste that makes the tablet agreeable to a woman to chew.

levonorgestrel, ethynodiol diacetate, norgestrel, norgestimate, gestodene, drospirenone, trimegestone, levodesogestrel, gestodyne, and nesterone. Preferably, the progestin is norethindrone.

The dosage of the oral contraceptive agent employed would tend to be that conventionally used in the art for the particular oral contraceptive agent selected. The proportion of the oral contraceptive agent in the tablet may be a pharmaceutically effective trace amount to about 10% by weight. Thus, the quantity of oral contraceptive agent per tablet may be varied as desired, typically about 10 micrograms to about 5 milligrams, but the lower and upper dosages may be reduced or increased. Examples of approximate dosage ranges of oral contraceptive agents in milligrams per tablet are summarized in Table 1.

TABLE 1

Examples of Dose Ranges of Oral Contraceptive Agents (milligrams per tablet)

| Description | Examples | Broad | Intermediate | Preferred |
| --- | --- | --- | --- | --- |
| Progestin | Norethindrone, | 0.1 to 2.5 | 0.25 to 2.0 | 0.4 to 1.5 |
|  | Norethindrone acetate | 0.1 to 2.5 | 0.25 to 2.0 | 0.4 to 1.5 |
|  | Desogestrel | 0.05 to 0.5 | 0.1 to 0.3 | 0.1 to 0.2 |
|  | Levonorgestrel | 0.025 to 1.5 | 0.025 to 1.0 | 0.05 to 0.6 |
|  | Ethynodiol diacetate | 0.5 to 2.5 | 0.75 to 1.25 | 0.9 to 1.1 |
|  | Norgestrel | 0.05 to 3.0 | 0.05 to 2.0 | 0.1 to 1.2 |
|  | Norgestimate | 0.1 to 0.5 | 0.15 to 0.35 | 0.18 to 0.25 |
|  | Gestodene | 0.03 to 0.15 | 0.05 to 0.10 | 0.06 to 0.075 |
|  | Drospirenone | 1.0 to 5.0 | 2.0 to 4.0 | 2.5 to 3.5 |
|  | Trimegestone | 0.05 to 0.5 | 0.1 to 0.3 | 0.1 to 0.2 |
| Estrogen | Ethinyl Estradiol, | 0.01 to 0.075 | 0.015 to 0.05 | 0.020 to 0.050 |
|  | Estradiol | 0.5 to 4.0 | 1 to 3 | 1.5 to 2.5 |
|  | Estradiol valerate | 0.5 to 5.0 | 1.5 to 3.5 | 1.9 to 3.0 |
|  | Estradiol acetate | 0.5 to 5.0 | 1.5 to 3.5 | 1.8 to 3.0 |

A tablet is "chewable," as used herein, such that when the tablet is chewed, it breaks into smaller pieces that can be swallowed. This is in contrast to gum, for example, which does not break into smaller pieces when chewed.

Description of the Invention

The first aspect of the invention relates to a chewable, palatable oral contraceptive tablet comprising an oral contraceptive agent, a chewable carrier suitable for human consumption and not comprising a ferrocene compound. The tablet of this invention expressly does not contain a ferrocene compound. Ferrocene compounds are used in the treatment of anemia and it should not be assumed that all patients desiring an oral contraceptive agent are anemic. Administering ferrocene compounds when they are not needed can lead to iron poisoning. Additionally, ferrocene compounds may not be palatable when chewed.

In principle, virtually any oral contraceptive agent used in human medicine could be employed in accordance with the principles of the present invention. The oral contraceptive agent may be an estrogen, a progestin, or a combination of an estrogen and a progestin. In one embodiment, the oral contraceptive agent is an estrogen selected from the group consisting of ethinyl estradiol, estradiol, estradiol valerate, and estradiol acetate. Preferably, the estrogen is ethinyl estradiol.

In another embodiment, the oral contraceptive agent is a progestin selected from the group consisting of norethindrone, norethindrone acetate, desogestrel, In one preferred embodiment, the tablet comprises estrogen in the form of ethinyl estradiol in an amount of about 10 micrograms to about 75 micrograms. In another preferred embodiment, the tablet comprises progestin in the form of norethindrone in an amount of about 0.1 milligram to about 2.5 milligrams.

The invention also includes a tablet in which the oral contraceptive agent is a combination of an estrogen and a progestin. Preferably, the estrogen is ethinyl estradiol and the progestin is norethindrone. In a more preferred embodiment, the amount of ethinyl estradiol in the tablet is about 10 micrograms to about 75 micrograms and the amount of norethindrone in the tablet is about 0.1 milligram to about 2.5 milligrams.

The tablets of this invention can be used in conjunction with an oral contraceptive regimen. The regimen can comprise administering tablets on a daily basis for multiple consecutive days. As such, throughout the duration of the regimen the amount of oral contraceptive agent in the oral contraceptive tablets may remain constant, thereby comprising a uniphasic regimen. Additionally, the amount of oral contraceptive agent in the oral contraceptive tablets may vary throughout the duration of the regimen, thereby comprising a multiphasic regimen. In tablets comprising an estrogen and a progestin, the ratio of the estrogen to the progestin can be constant throughout the duration of the regimen. Additionally, the ratio of the estrogen to the progestin in the oral contraceptive tablets can vary throughout the regimen.

It is also possible to form placebo tablets which otherwise correspond in composition to the tablet of the present invention but are free of the oral contraceptive agent.

The oral contraceptive agent may be present in a carrier either in a dissolved or a uniformly suspended state. A carrier comprises all but the active oral contraceptive agent or agents and includes an inactive ingredient or a combination of one or more inactive ingredients. The carrier imparts chewable and palatable characteristics to the tablet and must be suitable for human consumption, that is, free of harmful amounts of any toxins or components that are adverse to humans. All ingredients in the carrier should be generally recognized as safe (GRAS), as determined by the Food and Drug Administration (FDA) or the Flavor and Extract Manufacturers' Association (FEMA). The carrier selected for the invention must be chewable and should not confer a disagreeable taste to the tablet. Thus, the carrier itself must be palatable. The primary ingredient of a carrier is one or more diluents. Non-limiting examples of diluents that can be used in accordance with this invention include microcrystalline cellulose, corn starch, modified starch, calcium carbonate, dicalcium phosphate, and poly-alcohol sugars such as dextrose, mannitol, sorbitol, xylitol, lactose, sucrose, and fructose. Many other diluents or other ingredients suitable as components of carriers for a chewable, palatable oral contraceptive tablet are available and would be well known to those skilled in the art in view of the present disclosure.

In another aspect of the invention, the tablet optionally further comprises at least one of a flavor agent, a sweetener, and a color agent. A flavor agent can be used to enhance the taste of the tablet, making the tablet more palatable than a tablet without a flavor agent. Spray dried flavor agents are preferred because they are easy to incorporate into a chewable tablet. Non-limiting examples of preferred flavor agents impart the following flavors: strawberry, wild berry, spearmint, wintergreen, black cherry, orange, orange cream, and lemon. The flavoring agents are readily available from many commercial sources. Exemplary compounds suitably used in preparing flavors are listed in G. Burdock, Ed., Fenaroli's Handbook of Flavor Ingredients, $3^{rd}$ edition, Volumes I and II, CRC Press, New York, 1995. Other flavors and flavoring agents suitable for the tablet would be well known to those skilled in the art in view of the present disclosure.

A sweetener can also be used to enhance to taste of the tablet, making the tablet more palatable than a tablet without a sweetener. Sweeteners include natural sugars and artificial sugar substitutes. Non-limiting examples of sweeteners that can be used in accordance with this invention include aspartame, sucralose, xylitol, sorbitol, mannitol, dextrose, sucrose, and fructose. Non-limiting examples of the amount of flavor agents or sweeteners that can be used in the tablet composition of the present invention are listed in Table 2. The amounts in Table 2 are given as percentage of the total tablet weight.

TABLE 2

Sweetener and Flavor Amounts Used in Chewable Oral Contraceptive Formulations

| Ingredient Type | Examples | Broad | Intermediate | Preferred |
| --- | --- | --- | --- | --- |
| Sweetener | Aspartame | 0.02 to 1.0% | 0.02% to 0.2% | 0.03% to 0.05% |
|  | Sucralose | 0.01 to 0.5% | 0.01% to 0.1% | 0.02 to 0.04% |
| Flavor Agent | Spearmint | 0.5 to 5% | 1 to 3% | 1.5 to 2.5% |
|  | Wintergreen | 0.5 to 5% | 1 to 3% | 1.5 to 2.5% |
|  | Wild berry | 0.1 to 3% | 0.2 to 1% | 0.3 to 0.5% |

Optionally, a color agent may be added to aid in tablet identification and to enhance the visual appearance of the tablet. A visually pleasing color enhances patient acceptance and thereby compliance with an oral contraceptive regimen. The color agent may be any that are well known to those in the tablet-making art in view of the present disclosure, and could be used in any amount to impart the desired color.

The tablet can be manufactured by standard pharmaceutical techniques of solid dose formulation, such as granulation and compression. These processes are well known to those skilled in the art of making tablets (See Lieberman, Lachman, and Schwartz, *Pharmaceutical Dosage Forms*, Volume 1, New York, 1989). During the granulation process, other ingredients typically used in tablet formulation for human consumption can be included, such as binders, lubricants, anti-adherents, glidants, disintegrants and fillers or other optional ingredients that do not adversely affect chewability or palatability of the tablet or its active oral contraceptive agent ingredient(s).

Binders aid the formation of granulated particles of active oral contraceptive agents and carrier ingredients. Non-limiting examples of binders include glucose, acacia, guar gum, gelatin, simple syrup, sucrose, sorbitol, starch, alginic acid, alginate salts, polyethylene glycol, polyvinylpyrrolidone, polymethacrylates, pregelatinized starch, and celluloses such as methylcellulose, sodium carboxymethylcellulose, hydroxypropylmethylcellulose, hydroxypropylcellulose, and ethylcellulose. A solution of binder is prepared (concentrations dependent on the particular binder used), and the binder solution is mixed with the other excipients to form the wet granulation. A binder such as polyvinylpyrrolidone (Povidone) is typically used in a solution of about 3% to about 15% by weight and is added to the other tablet ingredients resulting in a final formulation concentration of about 2% to about 5%. Similarly, cellulose derivatives are typically used in granulating solutions of about 5% to about 10% by weight and concentrations would be known to one skilled in the art of making tablets using wet granulation in view of the present disclosure.

Disintegrants facilitate breakup of the tablet after administration during chewing. Non-limiting examples of disintegrants include crospovidone, croscarmellose sodium, starches, corn starch, potato starch, modified corn starch, sodium starch glycolate, and pregelatinized starch. Disintegrants can be included in the tablet formulation in amounts generally less than about 25% of the tablet weight, preferably less than about 20%, and more preferably about 1 to about 20% (natural starches such as corn or potato starch), about 5 to about 10% (pregelatinized starch), and about 3 to 8% (modified corn starch). Crospovidone and croscarmellose sodium are used at levels of about 5% or lower.

As a final step in the manufacture of the tablet, a lubricant, an anti-adherent, and a glidant can be added to the tablet granulation. A lubricant facilitates tablet manufacture by reducing friction in the tablet die during compression and ejection. An anti-adherent prevents the tablet from sticking to the tablet punch and die wall. A glidant improves flow characteristics of the granulation. Non-limiting examples of a lubricant include stearates, such as magnesium, calcium, and sodium stearates, stearic acid, hydrogenated vegetable oils, waxes, talc, boric acid, sodium benzoate, sodium acetate, sodium chloride, DL-leucine, sodium oleate, sodium lauryl sulfate, magnesium lauryl sulfate, and CARBOWAX® (Union Carbide Chemicals & Plastics Technology Corp.) polyethylene glycols. Non-limiting examples of an anti-adherent include talc, corn starch, colloidal silicon dioxide, DL-leucine, sodium lauryl sulfate, and metallic stearates. Non-limiting examples of a glidant include talc, corn starch, and colloidal silicon dioxides such as CAB-O-SIL® (Cabot Corp.), SYLOID® (W.R. Grace & Co.), and AEROSIL® (Degussa). Some ingredients, such as talc, can contribute to the formulation with combined functions, acting as a lubricant, and an anti-adherent, and a glidant.

A lubricant is typically included in the tablet formulation in amounts less than about 10% of the tablet weight, preferably less than about 6%, and more preferably about 0.25 to about 2% (stearates, stearic acid, hydrogenated vegetable oil), about 1 to about 5% (talc, waxes, DL-leucine, CARBOWAX®, sodium lauryl sulfate), about 1 to about 2% (magnesium lauryl sulfate) and about 4 to about 6% (sodium chloride, sodium oleate, sodium benzoate, sodium acetate).

Anti-adherents are typically included in the tablet formulation in amounts generally less than about 15% of the tablet weight, preferably less than about 12%, and more preferably about 3 to about 10% (cornstarch, DL-leucine), about 1 to about 5% (talc), about 0.1 to about 0.5% (colloidal silicon dioxide) and less than about 1% (sodium lauryl sulfate, metallic stearates).

A glidant is typically included in the tablet formulation in amounts generally less than about 15% of the tablet weight, preferably less than about 12%, and more preferably less than about 5 to about 10% (corn starch), about 0.1 to about 0.5% (CAB-O-SIL®, SYLOID®), about 1 to about 3% (AEROSIL®), and about 5% (talc).

The chewable tablet generally is not coated with a film or sugar coating. However, thin tablet coatings of a type known to those skilled in making coated tablets can be used.

In one preferred embodiment of the invention, the oral contraceptive agent comprises norethindrone and ethinyl estradiol, the carrier comprises dicalcium phosphate, lactose monohydrate, and maltodextrin, and the tablet further comprises sucralose, a flavor agent, sodium starch glycolate, povidone, and magnesium stearate.

The overall size of the tablet may be any tablet size that incorporates the desired contraceptively effective amount of the oral contraceptive agent and the carrier and is still chewable and palatable. In a preferred embodiment, the size of the tablet is small, on the order of about 50 milligrams to about 300 milligrams. More preferably, the tablet weight is about 70 milligrams to about 120 milligrams, and most preferably, the tablet weight is about 90 milligrams to about 110 milligrams. A smaller tablet is more portable than a larger tablet and therefore more appealing to patients preferring to carry oral contraceptive pills on their person, particularly in blister packaging. Further, smaller tablets are more likely than larger tablets to be accepted as chewable. Therefore, smaller tablets are more likely to enhance a patient's compliance with an oral contraceptive regimen. The shape of the tablet of the present invention is not critical.

The hardness of the tablet may be any hardness that allows for tablet formation and that is still palatable and chewable. One aspect of the invention includes a tablet having a hardness sufficient for blister packaging while still remaining palatable and chewable. Blister packaging is common in the art of oral contraceptive tablet dispensing. In a preferred embodiment, the tablet of the invention has a hardness of about 5 kilopond (kp) to about 15 kp, and preferably about 7 kp to about 12 kp.

Another aspect of this invention relates to a method of human female oral contraception comprising providing a chewable, palatable oral contraceptive tablet comprising a contraceptively effective amount of an oral contraceptive agent, and a chewable carrier suitable for human consumption, and not comprising a ferrocene compound, and administering the tablet to a human female. The tablet is the tablet described above, and typically and preferably, a number of such tablets as part of a contraceptive regimen.

The tablet can be administered to the woman in a variety of ways. Typically, the tablet is administered once daily. The tablet routinely contains a contraceptively active amount of an oral contraceptive agent, and some tablets used in a regimen may be a placebo. The placebo tablets are administered on days where the oral contraceptive agent is not required. As such, the woman is administered a tablet every day to help maintain the contraceptive regimen of taking a daily tablet. For example, a dosage regimen may utilize about 21 to about 63 days of tablets containing the oral contraceptive agent followed by about 3 to about 7 days of tablets comprising a placebo. Preferably, the regimen entails administering tablets for total of about 24 to about 32 days, wherein tablets containing the oral contraceptive agent are administered for about 21 to about 25 days, followed by about 3 to about 7 days of placebo tablets not containing the contraceptive. In one preferred embodiment, the tablets are administered for a total of about 28 days.

As explained above, the contraceptive dosage in the tablets can be uniphasic or multiphasic.

Another aspect of this invention relates to a method of enhancing compliance with a human female oral contraceptive regimen involving oral contraceptive tablets, the method comprising providing chewable, palatable oral contraceptive tablets comprising a contraceptively effective amount of an oral contraceptive agent, and a chewable carrier suitable for human consumption, and not comprising a ferrocene compound, and administering the tablets to the human female in accordance with the contraceptive regimen.

In connection with this aspect of the invention, each tablet of the regimen preferably comprises a daily dosage of the oral contraceptive agent. As such, daily administration of one of the tablets would be part of the regimen. The chewable, palatable oral contraceptive of this invention allows the woman the convenience of ingesting the tablet in a manner that does not require taking the tablet with liquid, without chewing it. Therefore, the woman can take the tablet each day at a time and place that is suitable to her lifestyle. Ingesting the tablets at the same time of day on a daily basis enhances compliance with any given contraceptive regimen.

The regimen can comprise any number of days of administration of the tablets to the woman. In one preferred embodiment, the regimen comprises providing about 21 to about 63 tablets, each tablet comprising the daily dosage of the oral contraceptive agent, followed by about 3 to about 7 tablets, each comprising a placebo. Preferably, a total of about 24 to about 32 tablets are administered daily, wherein about 21 to about 25 tablets each comprising the oral contraceptive agent are administered, followed by about 3 to about 7 tablets each comprising a placebo. In one preferred embodiment, a total of about 28 tablets is administered.

The amount of the oral contraceptive agent through the duration of the regimen can remain constant or can be varied for tablets containing an oral contraceptive agent (rather than placebo tablets without an oral contraceptive agent). In one embodiment, the amount of the oral contraceptive agent is present in the same amount in the oral contraceptive tablets of the regimen, thereby comprising a uniphasic regimen. In another embodiment, the amount of the oral contraceptive agent is present in varying amounts in the oral contraceptive tablets of the regimen, thereby comprising a multiphasic regimen. In tablets comprising an estrogen and a progestin, the ratio of the estrogen to the progestin can be constant throughout the duration of the regimen. Alternatively, the ratio of the estrogen to the progestin in the tablets can vary throughout the regimen.

Any number of the tablets may be dispensed in any type of packaging commonly used in the art of tablet dispensing. Blister packages are often and preferably used for dispensing oral contraceptives. Blister packages are generally small and portable, usually and preferably containing the number of tablets required for a month of dosing. Many patients desiring oral contraceptive tablets find this method of dispensing convenient. In a preferred embodiment, the tablets for the oral contraceptive regimen of this invention are dispensed in a blister package. The packaging is preferably in the form of a 28-daily dosage units blister package comprising about 21 to about 25 tablets comprising the oral contraceptive agent and the remaining respective about 7 to about 3 tablets comprising a placebo.

A tablet made in accordance with the present invention may simply be chewed. This substantially reduces the existing barriers to compliance. The use of a chewable, palatable tablet in accordance with the present invention eliminates the need to incorporate liquid to facilitate swallowing and makes oral contraceptives more agreeable for patients who have difficulty or reluctance to swallowing tablets. The chewable, palatable tablets of this invention have a tablet size and hardness suitable for use in blister packaging and are synergistic with the existing design and intent of oral contraceptive package portability and convenience. Therefore, the oral contraceptive formulations of this invention, administered according to this invention, provide a method of enhancing compliance with a human female oral contraceptive regimen.

The invention will now be described in more detail with reference to the following specific, non-limiting examples.

Compositions that have been prepared in accordance with this invention are given in Examples 1–2. Additional examples of compositions that can be formulated in accordance with this invention are given in Examples 3–6.

EXAMPLE 1

Composition of a 90 milligram tablet

| Ingredient Type | Ingredient | Amount (milligrams/tablet) |
|---|---|---|
| Oral Contraceptive Agent | Norethindrone | 0.40 |
| Oral Contraceptive Agent | Ethinyl Estradiol | 0.035 |
| Diluent | Dicalcium Phosphate | 40.8 |
| Diluent | Lactose Monohydrate | 40.8 |
| Diluent | Maltodextrin | 0.16 |

EXAMPLE 1-continued

Composition of a 90 milligram tablet

| Ingredient Type | Ingredient | Amount (milligrams/tablet) |
|---|---|---|
| Sweetener | Sucralose | 0.02 |
| Flavor Agent | Spearmint | 1.8 |
| Disintegrant | Sodium starch glycolate | 4.1 |
| Binder | Povidone | 1.5 |
| Lubricant | Magnesium stearate | 0.41 |

One technique of making the tablets of the present invention is a wet granulation technique. In a wet granulation technique, the active oral contraceptive agents are blended in a solution of binder which is then blended with the diluent(s) to form a wet granulation. After drying, the granulation is blended with the flavor ingredient(s), the disintegrant, the lubricant and any other optional ingredients. The final blend is compressed into tablets. This wet granulation method is exemplified by Examples 1 and 2.

Alternatively, a dry granulation technique can be used. In a dry granulation technique, the active oral contraceptive agents are blended with the diluent(s) to form a dry granulation. This is then blended with the flavor ingredient(s), the lubricant and any other optional ingredients, and finally compressed into tablets. This dry granulation method is exemplified by Examples 3, 4 and 5.

Alternatively, the active pharmaceutical ingredients are wet granulated as described previously, then blended with additional diluent(s) to form a dry granulation. This is then blended with the flavor ingredients, the lubricant and any other optional ingredients, and finally compressed into tablets. This method is exemplified by Example 6.

EXAMPLE 2

Composition of a 90 milligram tablet

| Ingredient Type | Ingredient | Amount (milligrams/tablet) |
|---|---|---|
| Oral Contraceptive Agent | Norethindrone | 0.40 |
| Oral Contraceptive Agent | Ethinyl Estradiol | 0.035 |
| Diluent | Dicalcium Phosphate | 40.8 |
| Diluent | Lactose Monohydrate | 40.8 |
| Diluent | Maltodextrin | 0.36 |
| Sweetener | Aspartame | 0.04 |
| Flavor Agent | Spearmint | 1.8 |
| Disintegrant | Sodium starch glycolate | 4.11 |
| Binder | Povidone | 1.54 |
| Lubricant | Magnesium stearate | 0.41 |

EXAMPLE 3

Composition of a 100 milligram tablet

| Ingredient Type | Ingredient | Amount (milligrams/tablet) |
|---|---|---|
| Oral Contraceptive Agent | Norethindrone | 0.40 |
| Oral Contraceptive Agent | Ethinyl Estradiol | 0.035 |
| Diluent | Dextrose | 97 |
| Flavor Agent | Spearmint | 2 |
| Lubricant | Magnesium stearate | 0.5 |

EXAMPLE 4

Composition of a 100 milligram tablet

| Ingredient Type | Ingredient | Amount (milligrams/tablet) |
|---|---|---|
| Oral Contraceptive Agent | Norethindrone | 0.40 |
| Oral Contraceptive Agent | Ethinyl Estradiol | 0.035 |
| Diluent | Mannitol | 97 |
| Flavor Agent | Strawberry | 2 |
| Lubricant | Magnesium stearate | 0.5 |

EXAMPLE 6

Composition of a 100 milligram tablet

| Ingredient Type | Ingredient | Amount (milligrams/tablet) |
|---|---|---|
| Oral Contraceptive Agent | Norethindrone | 0.40 |
| Oral Contraceptive Agent | Ethinyl Estradiol | 0.035 |
| Diluent | Dextrose | 60 |
| Diluent | Lactose | 37 |
| Flavor Agent | Strawberry | 2 |
| Lubricant | Magnesium stearate | 0.5 |

EXAMPLE 6

Composition of a 120 milligram tablet

| Ingredient Type | Ingredient | Amount (milligrams/tablet) |
|---|---|---|
| Oral Contraceptive Agent | Norethindrone | 0.40 |
| Oral Contraceptive Agent | Ethinyl Estradiol | 0.035 |
| Diluent | Dicalcium Phosphate | 20.8 |
| Diluent | Lactose Monohydrate | 20.8 |
| Diluent | Dextrose | 70 |
| Diluent | Maltodextrin | 0.16 |
| Sweetener | Sucralose | 0.02 |
| Flavor Agent | Spearmint | 1.8 |
| Disintegrant | Sodium starch glycolate | 4.1 |
| Binder | Povidone | 1.5 |
| Lubricant | Magnesium stearate | 0.41 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A chewable, palatable oral contraceptive tablet, comprising an oral contraceptive agent, a chewable carrier suitable for human consumption, wherein the contraceptive tablet is chewable and palatable and does not contain a ferrocene compound.

2. The tablet of claim 1, wherein the oral contraceptive agent is selected from the group consisting of an estrogen, a progestin, and a combination thereof.

3. The tablet of claim 2, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

4. The tablet of claim 1, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

5. The tablet of claim 1, wherein the oral contraceptive agent comprises an estrogen.

6. The tablet of claim 5, wherein the estrogen is selected from the group consisting of ethinyl estradiol, estradiol, estradiol valerate, and estradiol acetate.

7. The tablet of claim 6, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

8. The tablet of claim 1, wherein the oral contraceptive agent comprises a progestin.

9. The tablet of claim 8, wherein the progestin is selected from the group consisting of norethindrone, norethindrone acetate, desogestrel, levonorgestrel, ethynodiol diacetate, norgestrel, norgestimate, gestodene, drospirenone, trimegestone, levodesogestrel, gestodyne, and nesterone.

10. The tablet of claim 9, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

11. The tablet of claim 1, wherein the oral contraceptive agent comprises an estrogen and a progestin.

12. The tablet of claim 11, wherein the estrogen is selected from the group consisting of ethinyl estradiol, estradiol, estradiol valerate, and estradiol acetate, and the progestin is selected from the group consisting of norethindrone, norethindrone acetate, desogestrel, levonorgestrel, ethynodiol diacetate, norgestrel, norgestimate, gestodene, drospirenone, trimegestone, levodesogestrel, gestodyne, and nesterone.

13. The tablet of claim 12, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

14. The tablet of claim 13, further comprising at least one of a flavor agent, a sweetener, and a color agent.

15. The tablet of claim 1, wherein the tablet weighs about 50 milligrams to about 300 milligrams.

16. The tablet of claim 1, wherein the tablet has a hardness sufficient for blister packaging.

17. The tablet of claim 1, wherein the tablet has a hardness of about 5 kiloponds to about 15 kiloponds.

18. The tablet of claim 1, wherein the oral contraceptive agent comprises norethindrone and ethinyl estradiol, the carrier comprises dicalcium phosphate, lactose monohydrate, and maltodextrin, and the tablet further comprises sucralose, a flavor agent, sodium starch glycolate, povidone, and magnesium stearate.

19. A method of human female oral contraception, the method comprising providing a chewable, palatable oral contraceptive tablet comprising a contraceptively effective amount of an oral contraceptive agent, and a chewable carrier suitable for human consumption, and does not contain a ferrocene compound, and administering the tablet to a human female.

20. The method of claim 19, wherein the oral contraceptive agent is selected from the group consisting of an estrogen, a progestin, and a combination thereof.

21. The method of claim 20, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

22. The method of claim 19, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

23. The method of claim 19, wherein the oral contraceptive agent comprises an estrogen.

24. The method of claim 23, wherein the estrogen is selected from the group consisting of ethinyl estradiol, estradiol, estradiol valerate, and estradiol acetate.

25. The method of claim 24, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

26. The method of claim 19, wherein the oral contraceptive agent comprises a progestin.

27. The method of claim 26, wherein the progestin is selected from the group consisting of norethindrone, norethindrone acetate, desogestrel, levonorgestrel, ethynodiol diacetate, norgestrel, norgestimate, gestodene, drospirenone, trimegestone, levodesogestrel, gestodyne, and nesterone.

28. The method of claim 27, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

29. The method of claim 19, wherein the oral contraceptive agent comprises an estrogen and a progestin.

30. The method of claim 29, wherein the estrogen is selected from the group consisting of ethinyl estradiol, estradiol, estradiol valerate, and estradiol acetate, and the progestin is selected from the group consisting of norethindrone, norethindrone acetate, desogestrel, levonorgestrel, ethynodiol diacetate, norgestrel, norgestimate, gestodene, drospirenone, trimegestone, levodesogestrel, gestodyne, and nesterone.

31. The method of claim 30, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

32. The method of claim 31, wherein the tablet further comprises at least one of a flavor agent, a sweetener, and a color agent.

33. The method of claim 19, wherein the tablet weighs about 50 milligrams to about 300 milligrams.

34. The method of claim 19, wherein the tablet has a hardness sufficient for blister packaging.

35. The method of claim 19, wherein the tablet has a hardness of about 5 kiloponds to about 15 kiloponds.

36. The method of claim 19, wherein the oral contraceptive agent comprises norethindrone and ethinyl estradiol, the carrier comprises dicalcium phosphate, lactose monohydrate, and maltodextrin, and the tablet further comprises sucralose, a flavor agent, sodium starch glycolate, povidone, and magnesium stearate.

37. A method of enhancing compliance with a human female oral contraceptive regimen involving oral contraceptive tablets, the method comprising providing chewable, palatable oral contraceptive tablets comprising a contraceptively effective amount of an oral contraceptive agent, and a chewable carrier suitable for human consumption, and not comprising a ferrocene compound, and administering the tablets to the human female in accordance with the contraceptive regimen.

38. The method of claim 37, wherein the oral contraceptive agent is selected from the group consisting of an estrogen, a progestin, and a combination thereof.

39. The method of claim 38, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

40. The method of claim 37, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

41. The method of claim 37, wherein the oral contraceptive agent comprises an estrogen.

42. The method of claim 41, wherein the estrogen is selected from the group consisting of ethinyl estradiol, estradiol, estradiol valerate, and estradiol acetate.

43. The method of claim 42, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

44. The method of claim 37, wherein the oral contraceptive agent comprises a progestin.

45. The method of claim 44, wherein the progestin is selected from the group consisting of norethindrone, norethindrone acetate, desogestrel, levonorgestrel, ethynodiol diacetate, norgestrel, norgestimate, gestodene, drospirenone, trimegestone, levodesogestrel, gestodyne, and nesterone.

46. The method of claim 45, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

47. The method of claim 37, wherein the oral contraceptive agent comprises an estrogen and a progestin.

48. The method of claim 47, wherein the estrogen is selected from the group consisting of ethinyl estradiol, estradiol, estradiol valerate, and estradiol acetate, and the progestin is selected from the group consisting of norethindrone, norethindrone acetate, desogestrel, levonorgestrel, ethynodiol diacetate, norgestrel, norgestimate, gestodene, drospirenone, trimegestone, levodesogestrel, gestodyne, and nesterone.

49. The method of claim 48, wherein the carrier is selected from the group consisting of dicalcium phosphate, lactose, corn starch, microcrystalline cellulose, maltodextrin, dextrose, mannitol, sorbitol, xylitol, fructose, sucrose, and calcium carbonate.

50. The method of claim 49, wherein the tablets further comprise at least one of a flavor agent, a sweetener, and a color agent.

51. The method of claim 37, wherein each tablet weighs about 50 milligrams to about 300 milligrams.

52. The method of claim 37, wherein the tablets have a hardness sufficient for blister packaging.

53. The method of claim 37, wherein the tablet has a hardness of about 5 kiloponds to about 15 kiloponds.

54. The method of claim 37, wherein the oral contraceptive agent comprises norethindrone and ethinyl estradiol, the carrier comprises dicalcium phosphate, lactose monohydrate, and maltodextrin, and the tablet further comprises sucralose, a flavor agent, sodium starch glycolate, povidone, and magnesium stearate.

55. The method of claim 37, wherein each tablet comprises a daily dosage of the oral contraceptive agent.

56. The method of claim 55, wherein the regimen comprises providing about 21 to about 25 tablets comprising the oral contraceptive agent.

57. The method of claim 56, wherein the regimen further comprises about 3 to about 7 tablets comprising a placebo.

58. The method of claim 56, wherein the regimen is a uniphasic regimen wherein the oral contraceptive agent is present in the same amount in the tablets.

59. The method of claim 56, wherein the regimen is a multiphasic regimen wherein the oral contraceptive agent is present in differing amounts in the tablets.

60. The method of claim 37, wherein the tablets are provided in a blister package.

* * * * *